United States Patent
Gray

(10) Patent No.: US 9,533,117 B2
(45) Date of Patent: *Jan. 3, 2017

(54) LIMB FOR BREATHING CIRCUIT

(71) Applicant: Fisher & Paykel Healthcare Limited, Auckland (NZ)

(72) Inventor: Nathan Lee Gray, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/477,608

(22) Filed: Sep. 4, 2014

(65) Prior Publication Data

US 2014/0373843 A1 Dec. 25, 2014

Related U.S. Application Data

(63) Continuation of application No. 12/275,710, filed on Nov. 21, 2008, now Pat. No. 8,905,082, which is a (Continued)

(30) Foreign Application Priority Data

Sep. 9, 2002 (NZ) ........................................ 521274

(51) Int. Cl.
*F16L 11/00* (2006.01)
*A61M 16/08* (2006.01)
(Continued)

(52) U.S. Cl.
CPC ......... *A61M 16/0883* (2014.02); *A61M 16/08* (2013.01); *A61M 16/0816* (2013.01); *A61M 16/1095* (2014.02); *B29C 47/0016* (2013.01); *B29C 47/0021* (2013.01); *B29C 53/36* (2013.01); *B29C 53/582* (2013.01); (Continued)

(58) Field of Classification Search
USPC .... 138/33, 122, 109, 110, 116, 125, DIG. 8; 128/204.17, 203.26
See application file for complete search history.

(56) References Cited

U.S. PATENT DOCUMENTS 2,917,568 A 12/1959 Moorman et al.
2,943,644 A 7/1960 Moseley
(Continued)

FOREIGN PATENT DOCUMENTS

AU 200143823 A1 11/2001
DE 199 49 283 A1 4/2001
(Continued)

OTHER PUBLICATIONS

Information Disclosure Statement Transmittal Letter submitted in U.S. Appl. No. 10/653,821, dated Dec. 5, 2003.
(Continued)

*Primary Examiner* — James Hook
(74) *Attorney, Agent, or Firm* — Knobbe Martens Olson & Bear LLP

(57) ABSTRACT

A limb for a breathing circuit manufactured from very thin walled polymer materials has an elongate axial reinforcing spine lying freely inside the conduit and fixed to each end connector. The spine is laterally compliant but axially stiff. The spine provides resistance to tensile and compressive loads on the conduit, including that induced by prevailing internal pressures.

20 Claims, 11 Drawing Sheets

Related U.S. Application Data continuation of application No. 10/653,821, filed on Sep. 3, 2003, now Pat. No. 7,469,719.

(51) Int. Cl.

| | | |
|---|---|---|
| *B29C 47/00* | (2006.01) | |
| *B29C 53/36* | (2006.01) | |
| *B29C 53/58* | (2006.01) | |
| *B29C 53/60* | (2006.01) | |
| *B29C 63/00* | (2006.01) | |
| *F16L 9/16* | (2006.01) | |
| *F16L 11/115* | (2006.01) | |
| *A61M 16/10* | (2006.01) | |
| *B29C 47/02* | (2006.01) | |
| *B29C 65/40* | (2006.01) | |
| *B29C 65/00* | (2006.01) | |

(52) U.S. Cl.
CPC ............ *B29C 53/60* (2013.01); *B29C 53/607* (2013.01); *B29C 63/0013* (2013.01); *F16L 9/16* (2013.01); *F16L 11/115* (2013.01); *A61M 2205/0216* (2013.01); *A61M 2207/00* (2013.01); *B29C 47/021* (2013.01); *B29C 65/40* (2013.01); *B29C 66/1122* (2013.01); *B29C 66/43* (2013.01); *B29C 66/4322* (2013.01); *B29C 66/4329* (2013.01); *B29C 66/49* (2013.01); *B29C 66/496* (2013.01); *B29C 66/71* (2013.01); *B29C 2053/365* (2013.01); *Y10S 138/08* (2013.01); *Y10T 29/49826* (2015.01)

(56) References Cited

U.S. PATENT DOCUMENTS

| | | | |
|---|---|---|---|
| 3,144,313 A | 8/1964 | Pfefferle | |
| 3,163,707 A | 12/1964 | Darling | |
| 3,188,117 A | 6/1965 | Press et al. | |
| 3,228,877 A | 1/1966 | Mahon | |
| 3,245,206 A | 4/1966 | Bonnet | |
| 3,292,346 A | 12/1966 | Adams | |
| 3,303,105 A | 2/1967 | Konikoff | |
| 3,307,330 A | 3/1967 | Niedzielski et al. | |
| 3,307,589 A | 3/1967 | Sheffield | |
| 3,349,806 A | 10/1967 | Roberts | |
| 3,367,850 A | 2/1968 | Johnson | |
| 3,434,471 A | 3/1969 | Liston | |
| 3,735,558 A | 5/1973 | Skarstrom et al. | |
| 3,735,559 A | 5/1973 | Salemme | |
| 3,856,051 A | 12/1974 | Bain | |
| 3,889,717 A | 6/1975 | Obadal et al. | |
| 3,891,556 A | 6/1975 | Richardson et al. | |
| 3,895,630 A | 7/1975 | Bachman | |
| 3,910,808 A | 10/1975 | Steward | |
| 3,963,856 A | 6/1976 | Carlson et al. | |
| 3,966,525 A | 6/1976 | Steward | |
| 4,000,759 A | 1/1977 | Higbee | |
| 4,007,737 A | 2/1977 | Paluch | |
| 4,048,993 A | 9/1977 | Dobritz | |
| 4,180,103 A | 12/1979 | Mollere | |
| 4,204,562 A | 5/1980 | Kelly | |
| 4,207,457 A | 6/1980 | Haglund et al. | |
| 4,265,235 A | 5/1981 | Fukunaga | |
| 4,265,239 A | 5/1981 | Fischer, Jr. et al. | |
| 4,295,496 A | 10/1981 | Bixby | |
| 4,327,775 A | 5/1982 | Tally | |
| 4,336,798 A | 6/1982 | Beran | |
| 4,337,800 A | 7/1982 | Carlson et al. | |
| 4,343,672 A | 8/1982 | Kanao | |
| 4,420,016 A | 12/1983 | Nichols | |
| 4,456,034 A | 6/1984 | Bixby | |
| 4,462,397 A | 7/1984 | Suzuki | |
| 4,463,755 A | 8/1984 | Suzuki | |
| 4,469,495 A | 9/1984 | Hiraizumi et al. | |
| 4,490,575 A | 12/1984 | Kutnyak | |
| 4,509,359 A | 4/1985 | Gedeon et al. | |
| 4,517,404 A | 5/1985 | Hughes et al. | |
| 4,606,380 A * | 8/1986 | Jartoux | 138/122 |
| 4,653,542 A | 3/1987 | Tascher | |
| 4,669,508 A | 6/1987 | Neaves | |
| 4,686,354 A | 8/1987 | Makin | |
| 4,698,890 A | 10/1987 | Neaves | |
| 4,705,543 A | 11/1987 | Kertzman | |
| 4,708,831 A | 11/1987 | Elsworth et al. | |
| 4,791,963 A | 12/1988 | Gronert et al. | |
| 4,808,201 A | 2/1989 | Kertzman | |
| 4,838,258 A | 6/1989 | Dryden et al. | |
| 4,844,719 A | 7/1989 | Toyomoto et al. | |
| 4,874,925 A | 10/1989 | Dickenson | |
| 4,875,908 A | 10/1989 | Kikukawa et al. | |
| 4,942,905 A | 7/1990 | Takemae et al. | |
| 4,967,744 A | 11/1990 | Chua | |
| 5,042,500 A | 8/1991 | Norlien et al. | |
| 5,046,531 A | 9/1991 | Kanao | |
| 5,160,511 A | 11/1992 | Lovelock | |
| 5,233,996 A | 8/1993 | Coleman et al. | |
| 5,246,254 A * | 9/1993 | LoJacono, Jr. | F16L 35/00 138/109 |
| 5,284,160 A | 2/1994 | Dryden | |
| 5,307,639 A | 5/1994 | Boissin | |
| 5,357,948 A | 10/1994 | Eilentropp | |
| 5,392,770 A | 2/1995 | Clawson et al. | |
| 5,454,061 A | 9/1995 | Carlson | |
| 5,461,122 A | 10/1995 | Yilgor et al. | |
| 5,501,212 A | 3/1996 | Psaros | |
| 5,526,849 A | 6/1996 | Gray | |
| 5,620,500 A | 4/1997 | Fukui et al. | |
| 5,637,168 A | 6/1997 | Carlson | |
| 5,640,951 A | 6/1997 | Huddart et al. | |
| 5,722,391 A | 3/1998 | Rosenkoetter et al. | |
| 5,798,013 A | 8/1998 | Brandenburger | |
| 5,848,223 A | 12/1998 | Carlson | |
| 5,894,839 A | 4/1999 | Rosenkoetter et al. | |
| 5,969,618 A | 10/1999 | Redmond | |
| 5,975,144 A | 11/1999 | Akedo et al. | |
| 5,983,896 A | 11/1999 | Fukunaga et al. | |
| 6,078,730 A | 6/2000 | Huddart et al. | |
| 6,105,620 A | 8/2000 | Haberl | |
| 6,148,818 A | 11/2000 | Pagan | |
| 6,167,883 B1 | 1/2001 | Beran et al. | |
| 6,367,510 B1 | 4/2002 | Carlson | |
| 6,394,145 B1 | 5/2002 | Bailly | |
| 6,432,169 B1 | 8/2002 | Kluwe et al. | |
| 6,523,538 B1 | 2/2003 | Wikefeldt | |
| 6,536,428 B1 | 3/2003 | Smith et al. | |
| 6,662,802 B2 | 12/2003 | Smith et al. | |
| 6,769,431 B2 | 8/2004 | Smith et al. | |
| 7,086,422 B2 | 8/2006 | Huber et al. | |
| 7,140,366 B2 | 11/2006 | Smith et al. | |
| 7,291,240 B2 | 11/2007 | Smith et al. | |
| 7,469,719 B2 | 12/2008 | Gray | |
| 7,566,486 B2 | 7/2009 | Bourgois et al. | |
| 7,849,885 B2 | 12/2010 | Olsen et al. | |
| 8,336,570 B2 * | 12/2012 | Cardona | 137/68.14 |
| 8,905,082 B2 * | 12/2014 | Gray | 138/109 |
| 2001/0054422 A1 * | 12/2001 | Smith | A61M 16/08 128/200.24 |
| 2002/0002976 A1 * | 1/2002 | Smith | A61M 16/08 128/203.16 |
| 2002/0195104 A1 | 12/2002 | Fini et al. | |
| 2003/0028139 A1 | 2/2003 | Inoue | |
| 2004/0045549 A1 | 3/2004 | Smith et al. | |
| 2004/0065335 A1 | 4/2004 | Huber et al. | |
| 2004/0079371 A1 | 4/2004 | Gray | |
| 2004/0081784 A1 | 4/2004 | Smith et al. | |
| 2004/0118401 A1 * | 6/2004 | Smith et al. | 128/204.17 |
| 2004/0250815 A1 * | 12/2004 | Scott | A61M 16/08 128/204.17 |
| 2005/0115622 A1 | 6/2005 | Bennett et al. | |

(56) References Cited

U.S. PATENT DOCUMENTS

| | | | |
|---|---|---|---|
| 2005/0247362 A1* | 11/2005 | Harcourt | F16L 11/127 138/125 |
| 2006/0081303 A1* | 4/2006 | Coleman | 138/125 |
| 2009/0126817 A1 | 5/2009 | Gray | |

FOREIGN PATENT DOCUMENTS

| | | |
|---|---|---|
| DE | 199 58 296 C1 | 9/2001 |
| EP | 0 557 040 A1 | 8/1993 |
| EP | 0 621 050 A2 | 10/1994 |
| EP | 1 153 627 A2 | 11/2001 |
| EP | 1 166 814 A2 | 1/2002 |
| EP | 1 396 276 A2 | 3/2004 |
| GB | 859 613 | 1/1961 |
| GB | 2 139 110 A | 11/1984 |
| JP | S62-236724 A | 10/1987 |
| JP | H05-052378 A | 3/1993 |
| JP | 2000-24111 A | 1/2000 |
| WO | WO 97/18001 A1 | 5/1997 |
| WO | WO 98/24500 A1 | 6/1998 |

OTHER PUBLICATIONS

Information Disclosure Statement Transmittal Letter submitted in U.S. Appl. No. 10/653,821, dated Dec. 10, 2003.
European Search Report issued in EP Application No. 03020200.6, dated Mar. 17, 2004.
Office Action issued in BR Application No. PI0303478-0, issued Jun. 18, 2013.
U.S. Appl. No. 09/850,797, filed May 8, 2001, Smith et al.
U.S. Appl. No. 10/622,755, filed Jul. 18, 2003, Smith et al.
U.S. Appl. No. 10/653,821, filed Sep. 3, 2003, Gray.
U.S. Appl. No. 10/656,574, filed Sep. 5, 2003, Smith et al.
U.S. Appl. No. 12/275,710, filed Nov. 21, 2008, Gray.
Three pages off the SympaTex website of some of the most common questions that are asked and some technical data on the SympaTex membrane; Dated Apr. 5, 2000.
One page off the Perma Pure Inc. website of the product brochure #104 of the New PD™ Series Gas Dryers; Dated May 2000.
Partial European Search Report issued in EP Application No. 01111359.4, dated May 14, 2003.

* cited by examiner

LIMB FOR BREATHING CIRCUIT

CROSS-REFERENCE

This patent application is a continuation of U.S. patent application Ser. No. 12/275,710, filed Nov. 21, 2008, now U.S. Pat. No. 8,905,082, issued Dec. 9, 2014, and entitled "LIMB FOR BREATHING CIRCUIT," which is a continuation of U.S. patent application Ser. No. 10/653,821, filed Sep. 3, 2003, now U.S. Pat. No. 7,469,719, issued Dec. 30, 2008, and entitled "LIMB FOR BREATHING CIRCUIT," which claims the benefit of New Zealand Patent Application No. 521274, filed Sep. 9, 2002. These applications are hereby incorporated by reference in their entirety. In addition, any and all applications for which a foreign or domestic priority claim is identified in the Application Data Sheet as filed with the present application are hereby incorporated by reference under 37 C.F.R. §1.57.

BACKGROUND TO THE INVENTION

The present invention relates to components for breathing circuits and in particular to limbs for breathing circuits.

SUMMARY OF THE PRIOR ART

In assisted breathing, particularly in medical applications, gases are supplied and returned through conduits. Such conduits are ideally light and flexible to ensure the greatest level of comfort for the patient.

As taught in our prior patent application AU 43823/01 thin membrane walls are particularly used in breathable membrane applications where the passage of water vapour through the membrane but not the passage of liquid water is desired.

Thin walled conduits may include helical or annular reinforcing ribs which improve resistance to crushing and pinching, while still allowing the conduit to be flexible in order to maintain patient comfort. A disadvantage of these types of flexible conduits is their lack of stiffness. The extremely thin walls of these types of conduits provide very little resistance to tensile, compressive or torsional forces. While annular or helical ribs, whether inside, outside or between layers of the conduit wall, do provide some longitudinal stiffness, these conduits are still prone to large axial displacements both compressive and tensile. This can lead to substantial internal volume changes under fluctuating breathing pressures, potentially significant enough to disrupt automated ventilation. Our prior art patent application taught provision of external longitudinal reinforcing in the form of a set of axial polymer threads bonded to the radial support bead. However these have the disadvantage of being easily caught or snagged.

A further disadvantage of very thin walled conduits is a reduced durability of the very thin membrane making up the walls of the conduit. The very thin membrane may be more susceptible to piercing from sharp objects and/or plastic deformation from tensile forces.

SUMMARY OF THE INVENTION

It is an object of the present invention to provide a limb for a breathing circuit, which will at least go some way towards improving on the above or which will at least provide the public and the medical profession with a useful choice.

Throughout this specification the term very thin walled conduit means a conduit where under the intended prevailing conditions the conduit would be subject to excessive axial compression, e.g. a conduit formed according to a method as described in U.S. Pat. No. 3,910,808 using a SYMPATEX film having a thickness less than 50 microns.

In one aspect the invention consists in a limb for a breathing circuit comprising:

a very thin walled conduit having a first end and a second end and a breathing gases pathway therebetween, a first connector fixed to said first end of said conduit, a second connector fixed to said second end of said conduit, and an elongate reinforcing member lying freely within said very thin walled conduit along a non-tortuous path from one end of said conduit to the other end of said conduit, and connected with said first connector and said second connector.

Preferably said connectors have a first end suitable for making connection with auxiliary equipment and a second end for making connection with a breathing conduit, and an annular shoulder between said first end and said second end, said second end extending along an axis and having a substantially circular cross section, and said second end having at least one protrusion on an outer surface for interlocking engagement with a helical rib of a breathing conduit.

In a further aspect the invention consists in a method for manufacturing a limb for a breathing circuit comprising:

providing a very thin walled breathing conduit having a first end and a second end, locating an elongate reinforcing member having a first and a second end, lying freely within said conduit along a non-tortuous path from one end of said conduit to the other end of said conduit, fixing a first end connector with a first end of said breathing conduit, and a first end of said elongate reinforcing member, and fixing a second end connector with said second end of said conduit and said second end of said elongate reinforcing member.

In a further aspect the invention may broadly be said to consist in a limb for a breathing circuit comprising:

a very thin walled conduit having a first end and a second end, a first connector fixed to said first end of said conduit, a second connector fixed to a second end of said conduit, and a braided sheath surrounding said conduit and being fixed at and around one end to said first connector and at and around its other end to said second connector.

In a further aspect the invention consists in a method for manufacturing a limb for a breathing circuit comprising:

providing a very thin walled breathing conduit having a first end and a second end, locating a reinforcing mesh having a first and a second end, over the outside of said breathing conduit, fixing a first end connector with a first end of said breathing conduit, and a first end of said reinforcing mesh, and fixing a second end connector with said second end of said conduit and said second end of said reinforcing mesh.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

The present invention relates to breathing conduits in general and in particular to methods of providing reinforcement for very thin walled conduits used to provide a closed pathway for delivering gases to a patient. Consequently the present invention finds application in breathing conduits fabricated from a variety of different materials and manufactured by a variety of different methods. The conduits may be single or multiple walled and may include breathable walls or portions of breathable wall.

As a corollary of material cost and/or breathability of the material it is preferred that the conduit wall be manufactured to have a very thin wall, so much so that the conduit wall membrane may be insufficiently sturdy to be self supporting. Spiral or helical or annular reinforcing members may be provided on the tubular membrane to provide support against crushing and pinching. The helical, spiral or annular supporting members may for example be formed from polymer plastic materials, such as the material used in the wall of the conduit or having the same base polymer. It has been found that breathing conduits such as those described above are extremely light, flexible and provide good crush resistance, however the conduits may also have reduced resistance to axial deformation. Due to the very thin polymer film forming the walls of the conduit, the resulting breathing circuit limb may have reduced axial stiffness and may be prone to expansion, and contraction along the axis of the conduit, due to axial or torsional forces. In use, axial forces arising from patient breathing may produce expansion and/or contraction along the length of the limb. In one aspect the present invention provides a breathing circuit limb with improved axial stiffness. In a further aspect the present invention provides a breathing circuit limb with improved torsional stiffness.

Very thin walled breathing conduits such as those described above can be fabricated by a number of different methods. The following describes several very thin walled conduits and associated methods of manufacturing very thin walled conduits to which the present invention may be applied.

Figure 1:
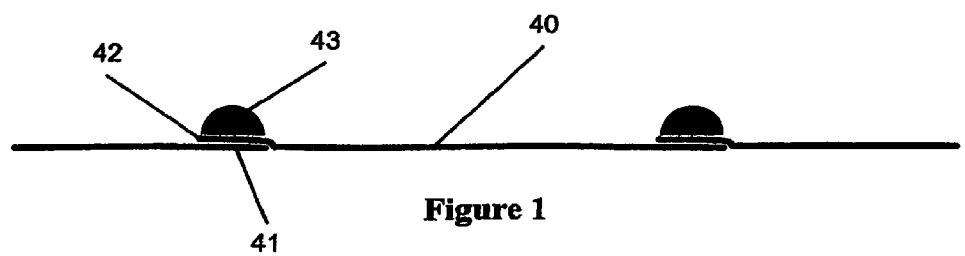
FIG. 1 is a cross sectional side elevation of a single walled breathing conduit formed by applying a molten reinforcing bead on top of overlapping spirally wound thin film layers.

Referring to FIG. 1 a cross section of the wall of a breathing circuit limb is shown in which the flexible wall of the conduit is formed from a very thin film plastic membrane, and wound helically with edges of adjacent turns welded together by a reinforcing bead. Supplied as tape, either pre-formed or extruded online, the very thin film 40 is wound helically onto a former with adjacent edges 41 and 42 of tape overlapping. A helical supporting rib 43, provided in a molten state is then laid on top of the overlap between adjacent turns. The helical supporting rib thermally and mechanically bonds the two adjacent strips with the rib forming a flexible resilient conduit once cooled. The resulting product is a single walled breathing conduit which is light and flexible. Further embodiments of conduits formed by such a process, such as multiple walled conduits, can be formed by adding further stages to the above described forming process.

Figure 2:
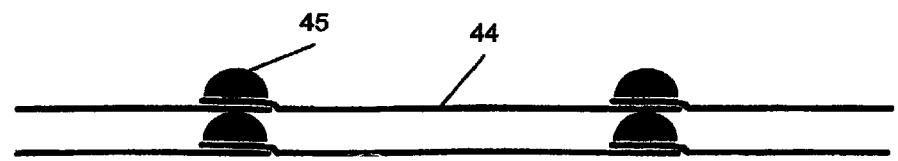
FIG. 2 is a cross sectional side elevation of a double walled breathing conduit formed in a manner analogous to the conduit shown in FIG. 1.

Referring to FIG. 2 a double walled conduit may be formed by adding an additional thin film layer 44 and supporting rib 45.

Figure 3:
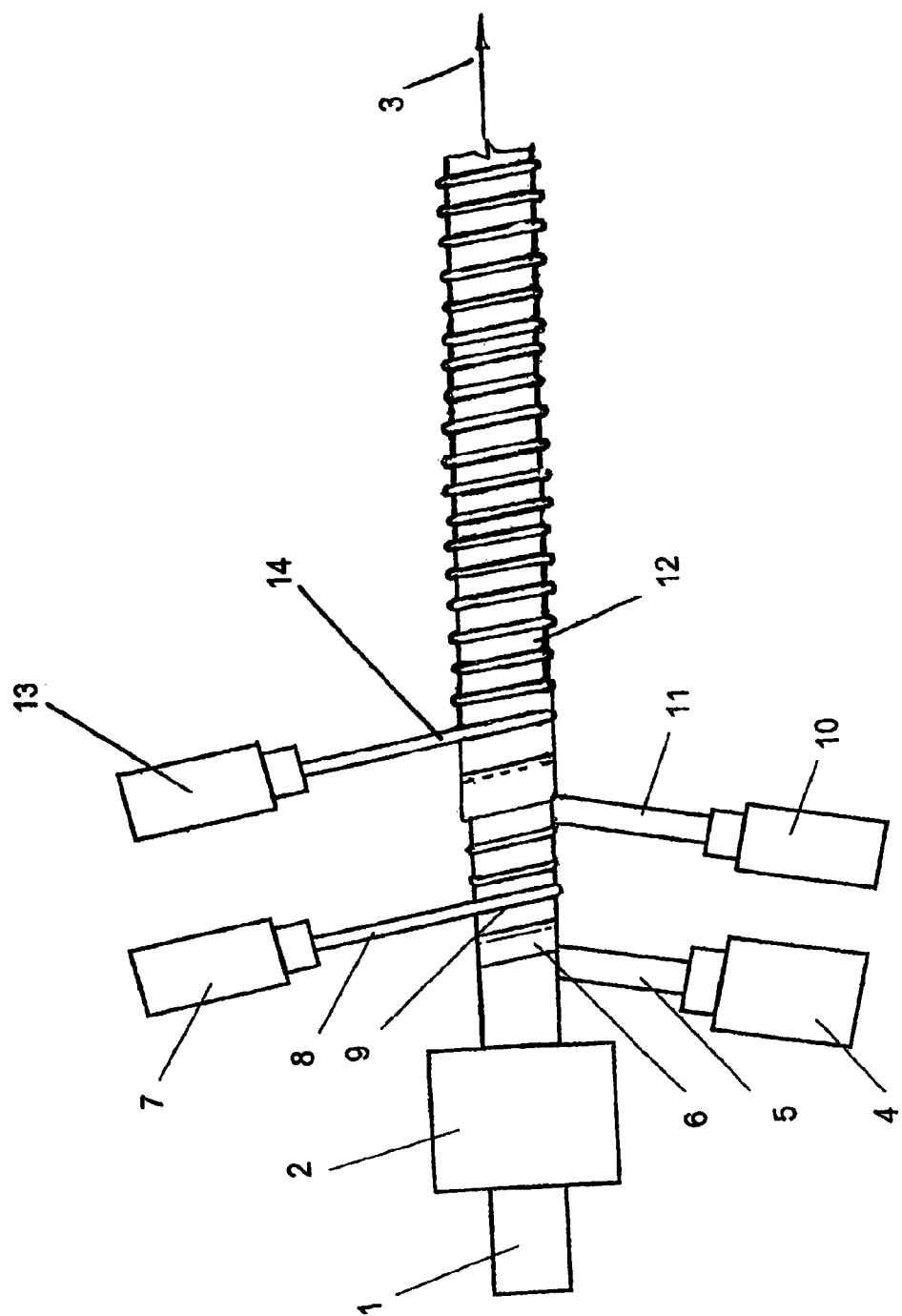
FIG. 3 is a plan view of a conduit forming device for forming the conduit depicted in FIG. 2.

An example of forming apparatus suitable for manufacturing the double walled breathing tube product according to the embodiment described in FIG. 2 is shown in FIG. 3. The apparatus includes a former 1 preferably of a known type including a plurality of rotating rods arranged around a central support rod. The rods extend from and are rotated by a gearbox within a machine stock 2. At least in the tube forming region the rotating rods follow a helical path. The pitch angle of the rods relative to the support rod controls the pitch angle of the tube being formed. An example of such a machine is a spiral pipeline mandrel available from OLMAS SRL of Italy. Tube being formed on the former is rotated and advanced in the direction of arrow 3 by the movement of the rotating rods. The advance speed of the former is selected relative to the rotational speed so that the pitch of the helical laying of the strip or tape on to the former 1 is a little less than the width of the strip so that adjacent turns narrowly overlap. A first extruder 4 extrudes a very thin tape 5 of breathable polymer materials. The tape 5 deposits on the former 1 in a helical fashion by action of the former. The pitch of the helical deposition of tape 5 is slightly less than the width of tape 5. The helical deposition of tape 5 forms the inner breathable wall 6 of the conduit. A second extruder 7 extrudes a bead 8 of polymer material. The bead 8 deposits on the former over the joint or overlap between adjacent turns of tape 5 forming a raised bead 9 along this join and welding the overlapping turns of tape 5. A third extruder 10 extrudes a second tape 11 of breathable polymer. The second tape 11 of breathable polymer is deposited on the former 1 to span between adjacent turns of bead 8. Adjacent turns of tape 11 overlap, forming outer breathable sheath 12. A fourth extruder 13 extrudes a second molten polymer bead 14. The bead 14 is helically deposited along the overlap between adjacent turns of the second tape 11 and welds the overlapping turns of tape 11. In addition to the bonding of the film overlap by application of the molten bead other active fusing techniques may be applied.

The resulting product is a double walled reinforced breathing conduit with a space between the inner and outer walls. The breathing conduit of FIG. 2 is manufactured by a method analogous to the method employed to manufacture the conduit of FIG. 1. The forming apparatus shown in FIG. 3 is effectively made up of two identical stages arranged in series.

The first stage of the former shown in FIG. 3 consists of film extruder 4 and bead extruder 7. Film 4 is wound around former 1 while extruder 7 extrudes a molten bead on top of the overlapping layers of film 5, resulting in a conduit such as that shown in FIG. 1. The second stage consists of film extruder 10 and bead extruder 13. This second stage effectively repeats the first stage over top of the conduit formed by the first stage and results in the double walled breathing conduit of FIG. 2.

Figure 4:
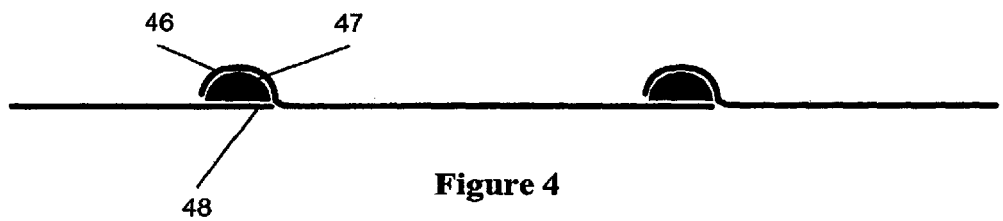
FIG. 4 is a cross sectional side elevation of a single walled breathing conduit formed by applying a molten reinforcing bead so that it resides between the overlapping spirally wound thin film layers.

Referring to FIG. 4, a conduit is shown according to another preferred method of manufacture of single walled breathing conduits. This method is particularly suited to very thin walled conduits and is the subject of a co pending patent application. The very thin film is arranged in a spiral or helix such that the edge portions of adjacent layers overlap and form the wall of a tube. Interposed the overlapping edges of adjacent winds of film is a bead of polymer material 47 bonded with the overlapping portions of film sealing the joint between windings and forming a continuous tube. The seam is formed between the edge of a first layer of film 48 and the edge of a second, adjacent layer of film 46 which is laid over top of the polymer bead while the bead is molten. The overlapping layer of film because it is so thin, follows the contour of the bead very closely and results in a smooth inner conduit wall.

Figure 5:
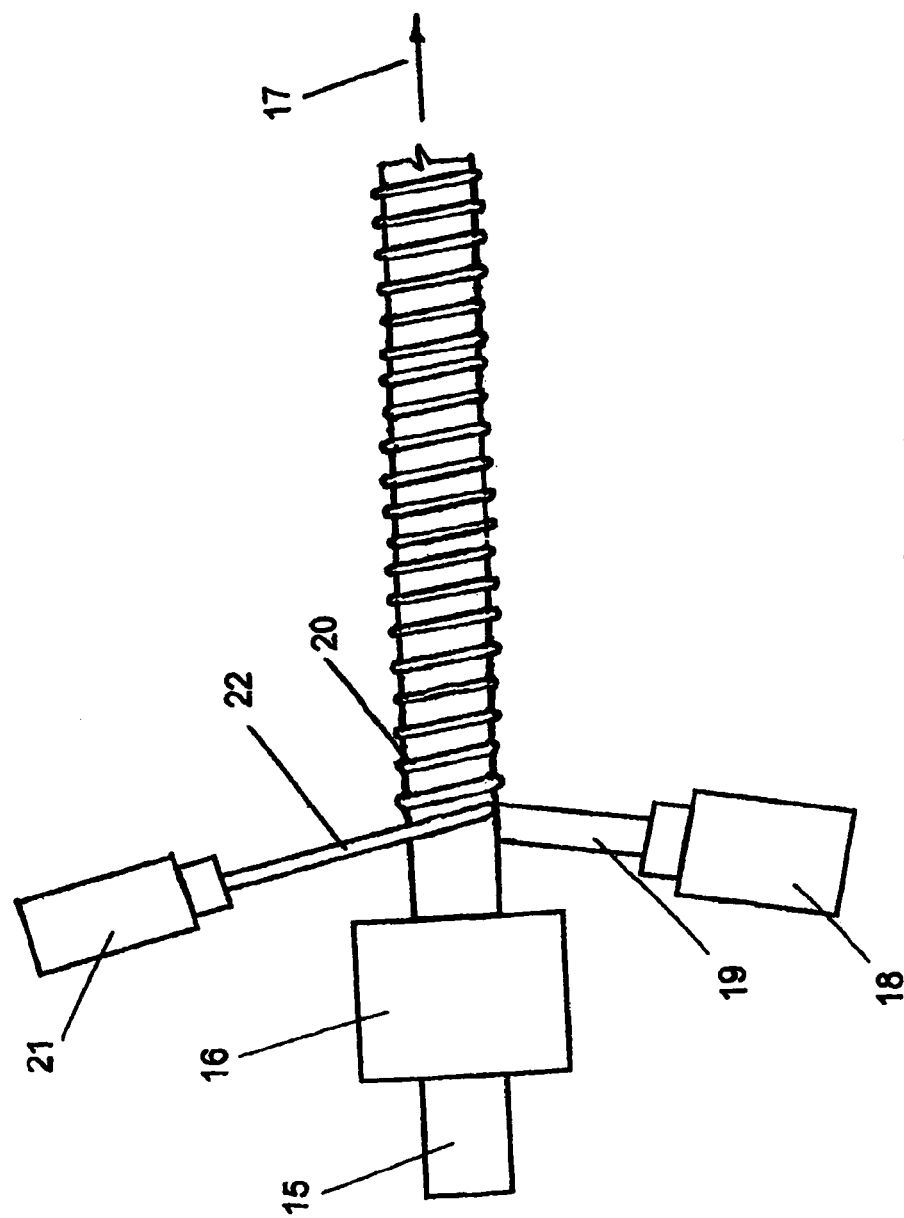
FIG. 5 is a plan view of a conduit forming device for forming the conduit depicted in FIG. 4.

An example of forming apparatus suitable for manufacturing the breathing tube according to an embodiment of the present invention described in FIG. 4 is shown in FIG. 5. The apparatus includes a former 15 including a plurality of rotating rods arranged around a central support rod. The rods extend from and are rotated by a gearbox within a machine stock 16. At least in the tube forming region the rotating rods follow a helical path. The pitch angle of the rods relative to the support rod controls the pitch angle of the tube being formed. An example of such a machine is a spiral pipeline mandrel available from OLMAS SRL of Italy.

Tube being formed on the former is rotated and advanced in the direction of arrow 17 by the movement of the rotating rods. The advance speed of the former is selected relative to the rotational speed so that the pitch of the helical laying of the strip or tape on to the former 15 is a little less than the width of the strip so that adjacent turns narrowly overlap. A first extruder 18 extrudes a tape 19 of very thin film polymer materials. The tape 19 deposits on the former 15 in a helical fashion by action of the former. The pitch of the helical disposition of tape 19 is slightly less than the width of tape 19. The helical deposition of tape 19 forms the wall 20 of the conduit. A second extruder 21 extrudes a bead 22 of polymer material. The molten bead 22 deposits between the overlapping portions of adjacent winds of tape 19 and is sufficiently heated to weld to the strips of tape 19. Applying the molten bead between the overlapping layers of tape may improve the weld quality as both layers of tape that are to be welded are in physical contact with the molten bead. The quality of the surface finish for the inner surface of a breathing conduit is important, as a rough inner surface may hinder gases flow and contribute to more condensation to building up in the conduit. The above described construction technique is especially suited to conduits fabricated from very thin film. The thin film is able to conform to the shape of the raised rib of the applied molten bead 22 during fabrication. By lapping very closely onto the bead and wrapping around the bead, the very thin film maintains a smooth inner surface on the finished conduit product as shown in FIG. 4.

In addition to the bonding of the film to the molten bead between adjacent over lapping layers, other active fusing techniques may be applied. Active methods may include hot air welding, hot rollers or radio frequency welding.

It will be appreciated that the above described breathing conduits and methods of manufacture are provided as examples of the type of very thin walled conduits to which the present invention may be applied. The examples have been chosen to illustrate the many possible variations and are not meant to be in any way limiting. Many further variations will present themselves to those skilled in the art. While some embodiments of the present invention have been described as preferred and convey particular advantages over other embodiments many other combinations may prove commercially useful.

Such variations may include:
(a) the utilisation of breathable material for the conduit walls or parts of the walls;
(b) single walled or multiple walled conduits, with or without space between the walls may be formed by adding extra stages to the forming process;
(c) single layer or multiple layer walls;
(d) very thin tape may be extruded at the time of forming, or pre-formed and supplied to former on reels;
(e) very thin tape may be provided as a laminate having a very thin film layer and a reinforcing layer which is also permeable to water vapour;
(f) forming process may include a secondary thermal welding process;
(g) molten bead may interpose layers or be applied on top of two or more layers;
(h) direct extrusion or drawing or blowing of a conduit;
(i) forming a conduit from a very thin film with a longitudinal seam;
(j) providing a series of annular radial support beads rather than a helical radial support bead.

The present invention may be broadly described as relating to methods of reinforcing breathing circuit limbs so as to provide increased axial or torsional stiffness, or both. While the present invention is particularly suited to conduits having very thin walls, it will be readily appreciated that application may also be found in more traditional conduits if further reinforcement is desirable. The first preferred embodiment of the present invention describes the provision of an axial spine and end connector whose primary function is to improve the axial stiffness of a breathing circuit limb. The second preferred embodiment of the present invention describes an external reinforcing sheath or mesh and an end connector for use with such reinforcing in a breathing circuit limb. The reinforcing mesh is bonded to the limb at only the ends of the limb where the conduit wall inserts into the end connector. It will be appreciated from the following description that the end connectors described are suitable for use with either one, or both, of the preferred embodiments of the present invention. While each embodiment of the present invention is discussed in turn, it is in no sense meant to be limiting as the preferred embodiments may be employed separately or together.

A first preferred embodiment of a breathing limb according the present invention will be described in detail with reference to FIGS. 6 to 8. The breathing limb has a conduit end connector 23 (or 49), suitable for connecting a breathing conduit with a device, for example a gases humidification device or ventilator or mask. A first end of end connector 23 is configured to mate with auxiliary equipment such as a ventilator or mask, while the second end is configured to extend into a breathing conduit. The end view cross section of each end portion of the connector is substantially circular. Between the two ends of the end connector 23 is a shoulder region which makes the transition between the respective diameters of the connector ends. Preferably the shoulder portion has an annular recess 32, for receiving a securing collar or retaining sleeve 29.

The limb includes an elongate reinforcing member or spine 24 lying freely within conduit 25. Conduit 25 for example, is such as those described above. The second end of conduit end connector 23 has a recess 26 adapted to receive an elongate reinforcing spine or rod 24. The spine 24, runs the length of the conduit from the connector 23 at one end of the tube, down the inside of the conduit, and is secured in another end connector 49 at the other end of the conduit. Preferably the spine is substantially the same length as the conduit and follows a non-tortuous path between the connectors. Because the spine (between the connectors) is preferably slightly longer than the conduit, it will not follow a linear path, but rather will bend into a shallow wavy and/or spiral form. It will also be appreciated that a spine slightly shorter than the conduit will also result in a degree of axial reinforcement. When assembled as described the combination of end connector and spine will provide the breathing conduit with additional axial stiffness, by potentially taking some of the axial forces and will therefore go some way to overcoming the above described disadvantages that arise from the use of breathing conduits having extremely thin film walls. In this embodiment it is preferable to choose the reinforcing spine (material, gauge and number) to be sufficiently stiff to resist buckling under the transiently reduced internal pressures that could be expected during patient breathing and sufficiently stiff to provide improved axial stiffness to the conduit. Preferably the elongate reinforcing member is manufactured from high density polyethylene having a Young's modulus (E), of approximately 0.88 GPa. Preferably the elongate reinforcing member has a cross sectional are between 3 mm$^2$ and 12.5 mm$^2$. Preferably the elongate reinforcing member has a minimum bending stiffness (EI=Young's Modulus*Second Moment of Area) for its cross section between 693 N·mm$^2$ and 11,096 N·mm$^2$.

Although embodiments containing only one elongate reinforcing spine are shown, it will be appreciated by those skilled in the art that the end connectors described could easily be modified to accommodate multiple reinforcing spines. In such multi-spine embodiments, care needs to be taken to ensure that the gases flow is not disrupted too detrimentally. A further important consideration when choosing the material, gauge and number of reinforcing members is to ensure that the breathing circuit limb remains laterally flexible and thus maintain patient comfort.

The reinforcing spine is preferably made from a suitable approved plastic material, such as high density polyethylene, or the same material as the end connectors if welding of the spine and end connectors is selected for manufacture. In the preferred embodiment the reinforcing spine has a circular cross section to minimise any potential stress raisers. The spine may be made from a variety of materials, and may have a variety of cross sections being either solid or hollow without departing from the spirit of the present invention. Preferably in hollow spine embodiments the spine is blind terminated at each end by the end connectors. If the spine is hollow and has a narrow bore, the size of the bore will be insufficient for general gases flow or gases delivery. The cross sectional area of the spine (measured from the outer perimeter of the cross section of the spine) is preferably less than 10% of the cross sectional area of the bore of the conduit so that gases flow is not significantly disrupted. While the spine diameter is not large enough to facilitate significant gases flow (to a patient for example) it may be used for other purposes such as pressure measurement, or pressure feedback. The spine may also include a heater element such as a PTC (Positive Temperature Coefficient) heater or a resistance heating element.

It is envisaged that there are several possible variants which may be employed to secure the reinforcing spine and/or reinforcing mesh into each of the end connectors of the breathing circuit limb. The general requirements for the end connectors are as follows. The end connectors must provide a means for securely fastening the spine and/or reinforcing mesh so as to prevent pull out during use. Preferably the end connectors are constructed such that assembly of the components during manufacture can be achieved easily. A further consideration is that the end connector when fastened to a breathing conduit to form the finished product should be neat, tidy and preferably appealing to the eye of an end user. The following describes two alternative preferred embodiments of the present invention which attempt to satisfy the abovementioned design objectives. It will be appreciated that the portion of the end connector described which connects to equipment such as a ventilator or mask may be male, female or an androgynous type connector without departing from the present invention. Further, each end of a conduit may have the same or a different type of connector according to what type of connection is required. If a heater wire is included in the breathing circuit limb (whether associated with the reinforcing spine or not) the end connector at at least one end will preferably be adapted to make an electrical connection together with the gases pathway connection.

Figure 6:
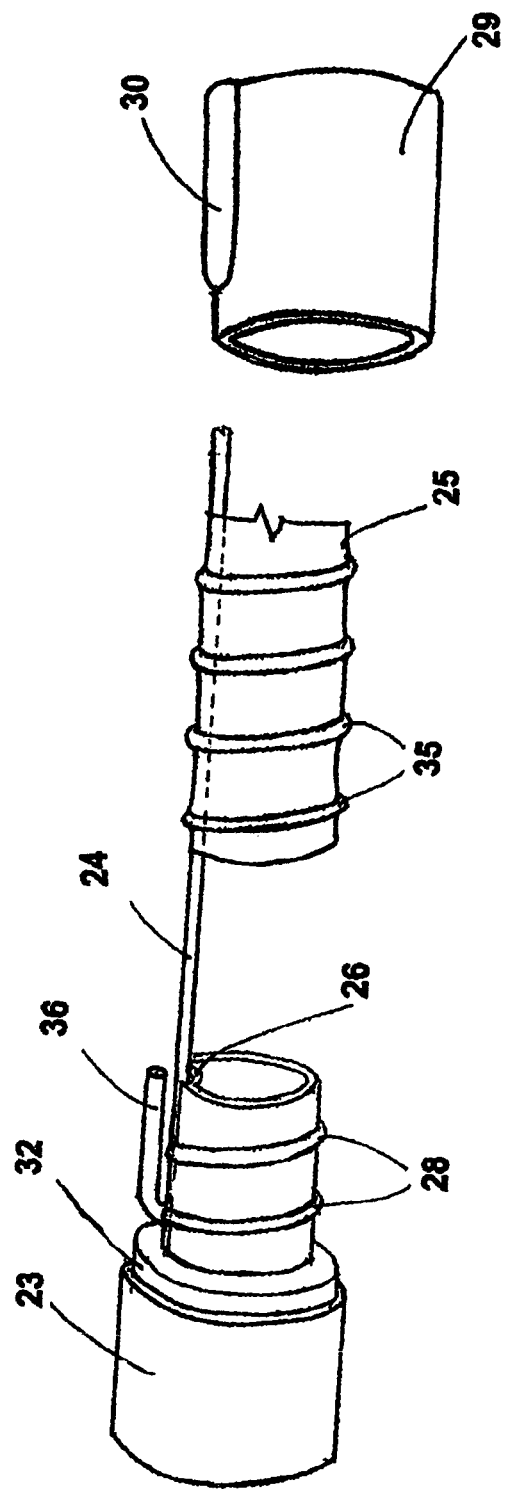
FIG. 6 is an assembly perspective view of one end of a breathing limb according to a preferred embodiment of the present invention.
Figure 7:
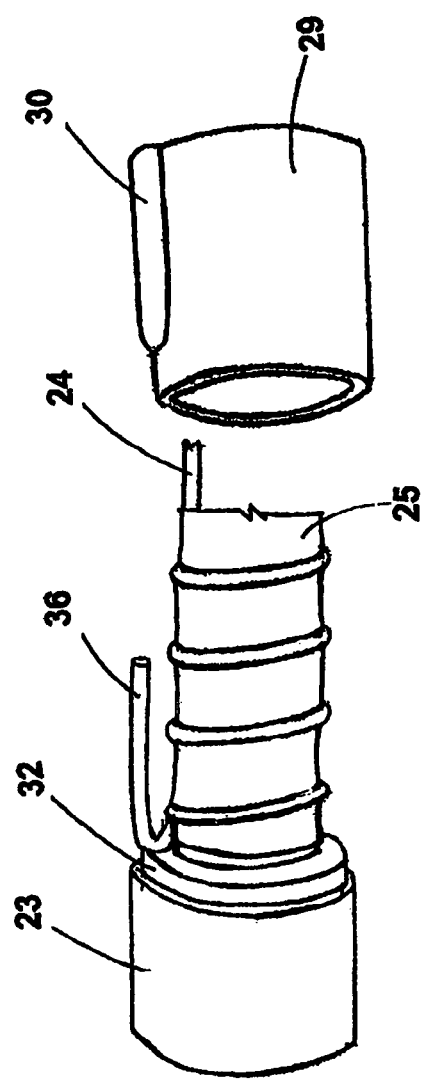
FIG. 7 is a partially assembled perspective view of the end of a breathing limb shown in FIG. 6.
Figure 8:
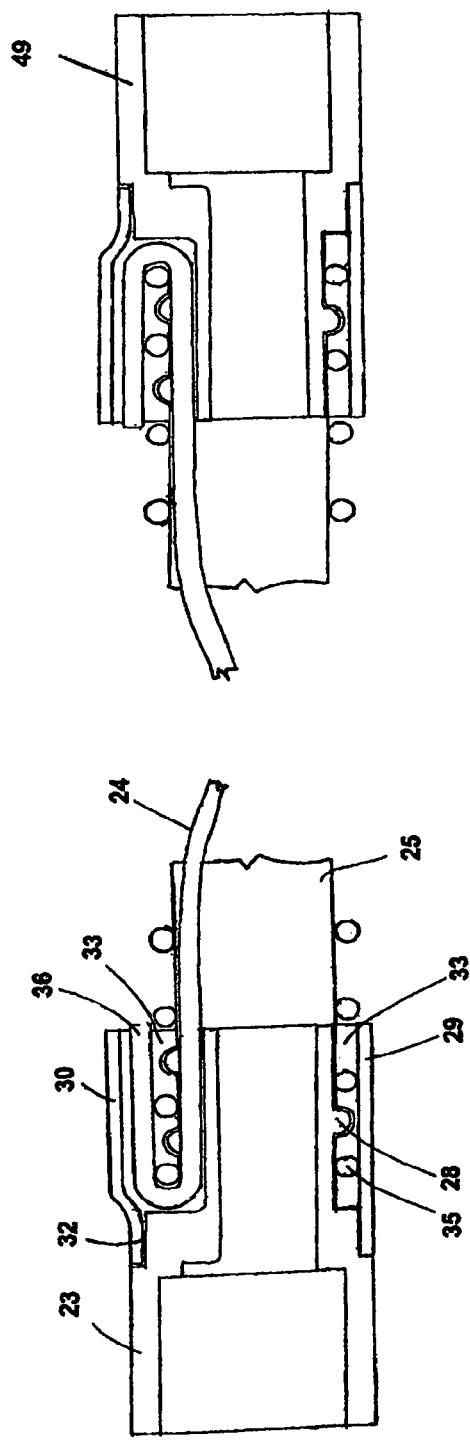
FIG. 8 is a cross-sectional elevation of the ends of the breathing limb according to FIGS. 6 and 7.

Referring to FIGS. 6 to 8, a connector according to a preferred embodiment of the present invention is shown. In order to provide a strong bond between the conduit and the connector, a portion of the connector which receives the conduit is provided with outer raised protrusions 28 to cooperate with the helical reinforcing bead of the conduit. The protrusions 28 are arranged to cooperate with the pitch of the conduits helical reinforcing bead and preferably take the form of a continuous thread. It will however be appreciated that the protrusions may be any number of discrete bumps arranged to cooperate with the conduit reinforcing bead. The raised thread 28 takes up a position between the adjacent turns of the helical reinforcing bead 35 of the conduit. The thin wall of the conduit between the reinforcing bead is able to deform if necessary to accommodate the raised external thread of the end connector locking the components together. These features provide a mechanical connection and resistance to the conduit being pulled from the connector. As shown in FIG. 6 the portion of the connector which receives the conduit is also provided with a recess or groove 26 for receiving the reinforcing spine 24. Preferably the recess 26 is substantially parallel with the extrusion axis of the connector. For assembly, the recess 26 provides a locating means for the reinforcing spine allowing the conduit to be threaded over the external raised thread on the receiving portion of the end connector. The reinforcing spine runs up the inside of the conduit and is received into recess 26 of the end connector. The spine then emerges from the recess 26 where an end portion 36 of the spine 24 is folded back on itself around the outside of the conduit wall. This feature provides a mechanical interlocking of the spine around the conduit wall as well as providing an end section of the spine that is in a position to be adhesively secured to the outer surface of the conduit wall.

In one preferred embodiment, illustrated in FIG. 6, a retaining sleeve or securing collar 29 is fitted over the assembled components. The securing collar 29, is substantially cylindrical about an extrusion axis. The retaining sleeve may include a raised portion 30 which results in a recess on the inside of the securing collar as shown in FIGS. 6 to 8 for receiving the end portion of the spine 24 which is folded back on itself on the outside of the breathing conduit. Alternatively a recess may be formed on the inner wall of the securing collar 29, without the presence of an external protrusion. Preferably the recess is substantially parallel with the extrusion axis of the securing collar. Alternatively, referring to FIG. 9 the end portion of the spine 36 may be folded so it lies between the helical reinforcing bead 35 of the conduit and the raised thread 28 of the end connector 23.

The assembly is secured via a tubular retaining or securing collar sleeve 31. The retaining sleeve 31 and end connector 23 may be provided with a positive initial location via a snap fit interaction between a snap fit portion 32 of the end connector 23 and the lip of retaining sleeve 31. Referring to FIGS. 6 to 9, a suitable adhesive such as EVA (Ethylene-Vinyl Acetate) glue can then be injected into the annular space 33 formed between the receiving portion of the end connector and the retaining sleeve. One or more small openings may be provided in the securing collar for the purpose of injecting glue into the annular cavity 33. The injected adhesive performs two functions, firstly the adhesive forms a seal between the conduit and the end connector. Secondly, the adhesive forms both an adhesive bond and a mechanical bond anchoring the conduit and spine to the end connector. The mechanical bond is formed between the raised external threads of the end connector and the cured glue which fills the annular space between the end connector and the retaining sleeve. The mechanical bond between the raised threaded portion of the end connector and the breathing conduit is an important feature because there may be no adhesive between these two surfaces. The cured glue must be hard enough to prevent the thin walled conduit and reinforcing bead from deforming far enough to allow the conduit to be pulled over the raised external thread.

Figure 9:
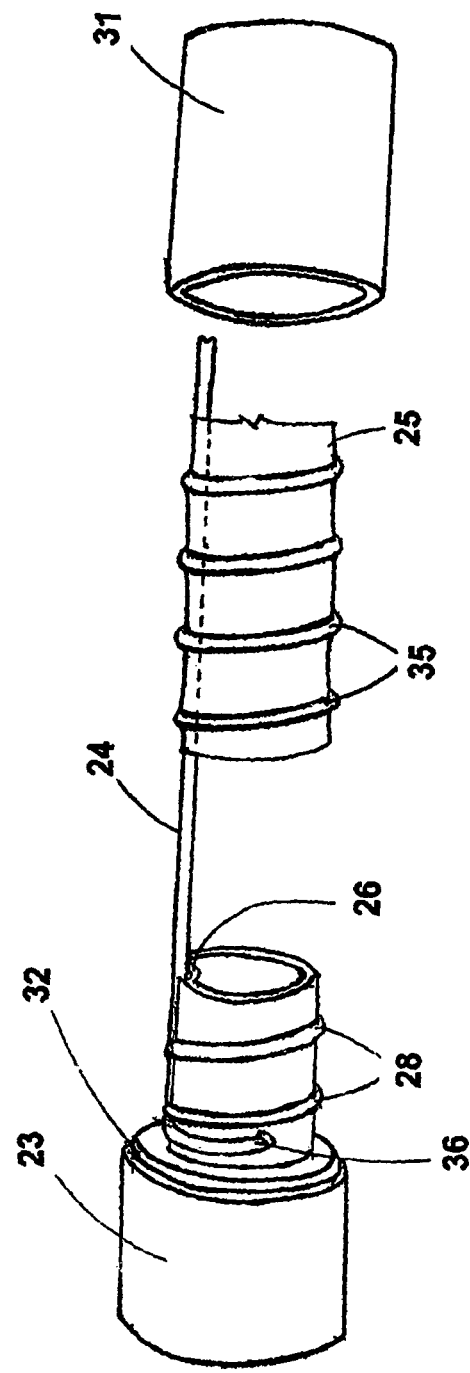
FIG. 9 is an assembly perspective view of one end of a breathing limb according to a further preferred embodiment of the present invention.
Figure 10:
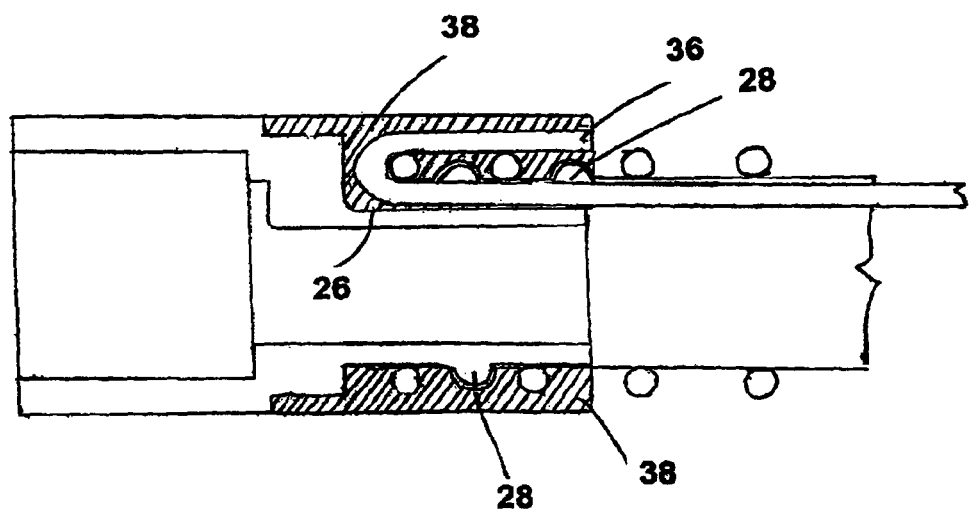
FIG. 10 is a cross-sectional elevation of a breathing limb according to a further preferred embodiment of the present invention.

An alternative preferred embodiment of an end connector will be described with reference to FIG. 10. An end connector as described previously with an external raised thread 28 on a conduit receiving portion of the connector is provided. In a similar manner to that described above the end connector is also provided with a recess 26 for receiving a reinforcing spine. During assembly the reinforcing spine is located in the recess before the helically ribbed breathing conduit is threaded over the reinforcing spine and receiving portion of the end connector. As described above, an end portion of the reinforcing spine 36 is folded over the outside of the breathing conduit wall in preparation for adhesive securing. Alternatively, end portion 36 may be positioned as shown in FIG. 9. The assembly is then inserted into an injection mould cavity so that a collar 38 (shown hatched) is overmoulded to perform the functions of securing and sealing as described above.

Due to the axial compliance of very thin walled conduits, the length of spine will contribute to the determination of the length of the limb. In the preferred embodiment the spine length is chosen such that when fitted inside the conduit and secured to the respective end connectors, the conduit is elongated such that the conduit length is close to its maximum length (preferably within the elastic limit of the conduit walls). In such a condition the wrinkling of the conduit wall is reduced, improving the performance of the breathing circuit limb without putting undue stress on the conduit wall due to axial tension generated by the spine. The axial stiffness of the conduit is improved while limb flexibility is not significantly impaired. For this condition, the spine is preferably between 100.5% and 105% of the length of the conduit.

Figure 11:
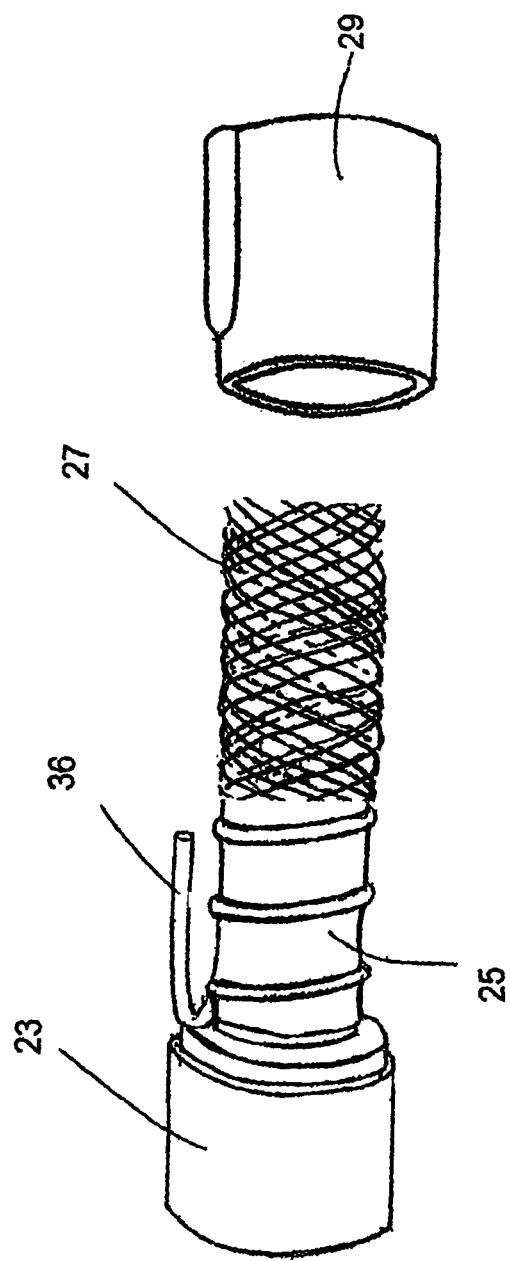
FIG. 11 is a partially assembled perspective view of one end of a breathing limb according to a further aspect of the present invention including an outer reinforcing mesh.
Figure 12:
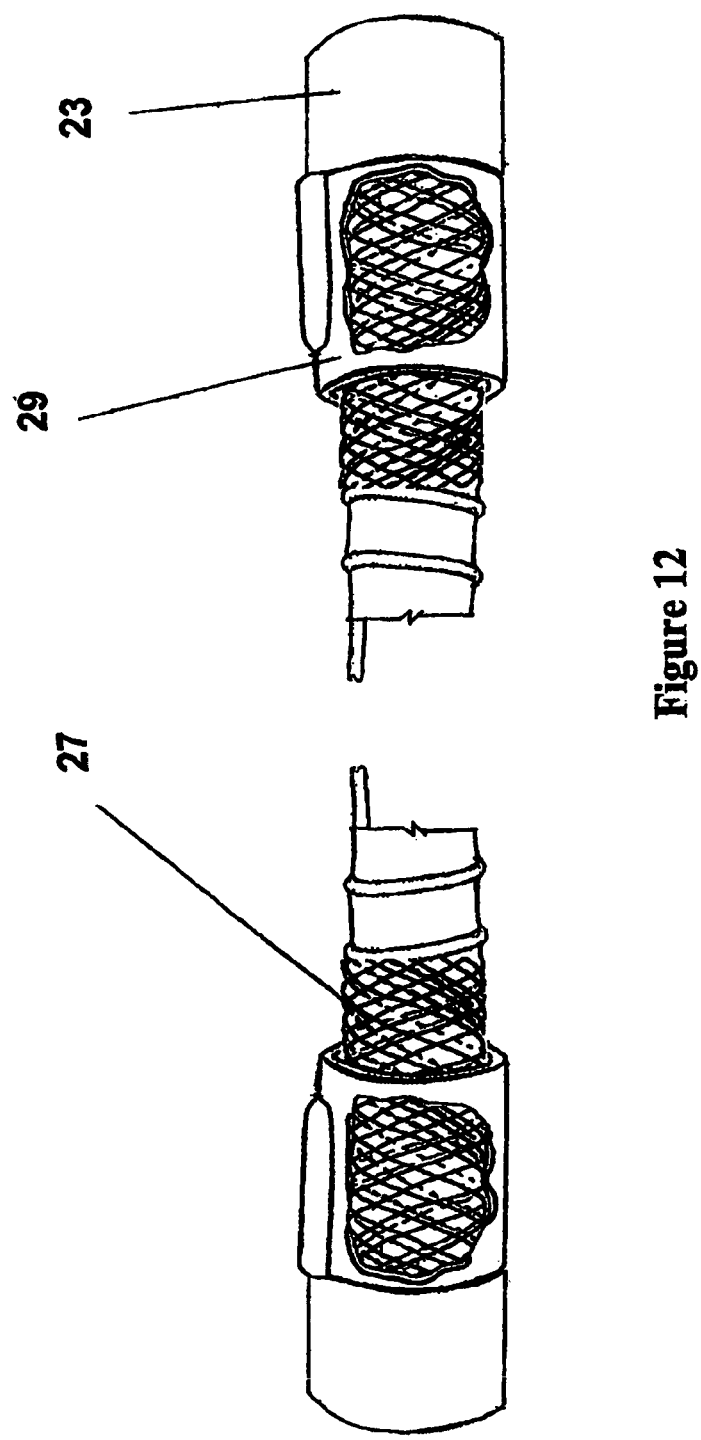
FIG. 12 is cutaway view of the breathing limb of FIG. 11 showing the outer reinforcing mesh fixed at and around the end connectors.

A second preferred embodiment of the present invention will now be described in detail with reference to FIGS. 11 and 12. FIG. 11 discloses a breathing circuit limb including an outer reinforcing sheath 27 covering the entire length of the breathing conduit.

The reinforcing sheath 27 is preferably a braided mesh surrounding the breathing circuit limb and is bonded to the limb only at the ends where the breathing conduit is inserted into the end connectors. All styles of breathing circuit limb end connector described above are suitable for receiving and securing a reinforcing mesh according to the second embodiment of the present invention. In each case the reinforcing sheath is located outside the breathing conduit wall and is secured at and around the end connector at the same time as the conduit wall is secured. FIG. 11 shows an end connector having a breathing conduit receiving portion which includes a raised external thread for cooperation with the helical reinforcing bead of the conduit. The end connector may also include a recess or groove for receiving a reinforcing spine as described in the first preferred embodiment of the present invention. During assembly the thin walled breathing conduit is threaded over the end connector conduit receiving portion via the interaction between the breathing conduits helical reinforcing bead and the end connectors raised external thread. A tubular braided reinforcing mesh 27 is then installed over top of the breathing conduit. FIG. 11 shows a reinforcing mesh 27 over a portion of breathing conduit. In FIG. 11, the end portion of the mesh is not yet pulled all the way over the conduit ready for securing via retaining collar 29.

As previously described in the first preferred embodiment of the present invention two preferred methods of securing the breathing circuit limb components are disclosed. The first method employs a securing collar positioned over the breathing conduit and the conduit receiving portion of the end connector, forming an annular space which is then filled with a suitable adhesive such as EVA glue. The alternative securing method described in the first preferred embodiment of the present invention may be adapted to secure the braided reinforcing sheath into the end connector. In this overmoulded alternative the assembled components are inserted into an injection mould cavity so that a collar may be overmoulded to perform the functions of securing and sealing the components of the breathing circuit limb. In this method the retaining sleeve is substituted for the overmoulded resin.

The braided reinforcing mesh may be applied to a breathing conduit as an online process where the braid is formed at the same time as the conduit is formed, or alternatively a prebraided tube may be applied to a breathing conduit in a separate process. The braided mesh may be fabricated from a variety of materials but is preferably polyethylene terephthalate monofilaments.

In use the braided sheath contributes significantly to the tensile and torsional stiffness of the breathing circuit limb. While there is no bonding between the reinforcing mesh and the breathing circuit limb along the length of the conduit, it has been found that the braided reinforcing mesh significantly improves torsional rigidity of the breathing circuit limb. In this embodiment it is preferable to choose the material, number, weave pitch and gauge of the braided filaments to improve the conduits stiffness. When the limb is loaded in tension, the stretching of the reinforcing mesh causes the mesh tube to constrict radially. This radial constriction is resisted by the helical reinforcing bead of the breathing conduit resulting in a strain limiting effect for the breathing circuit limb. This effect significantly improves the breathing circuit limb strength and stiffness against axial tensile forces. The outer mesh sheath also provides an additional advantage by reducing direct contact between the user/environment and the outer surface of the breathing conduit tube, therefore reducing the risk of puncture and damage. This feature significantly improves the durability of the breathing circuit limb, and is especially suitable for conduits with very thin walls, such as those which may be found in breathable walled limbs.

The invention claimed is:

1. A limb for a breathing circuit comprising:
   a flexible conduit having a first end and a second end and a breathing gases pathway therebetween, said flexible conduit formed using a film having a thickness less than 50 μm,
   a first connector fixed to said first end of said flexible conduit,
   a second connector fixed to said second end of said flexible conduit, and
   an elongate reinforcing member lying freely within said flexible conduit along a non-tortuous path from one end of said flexible conduit to the other end of said flexible conduit, and connected with said first connector and said second connector, such that said elongate reinforcing member reinforces said flexible conduit against contraction along the length of said flexible conduit due to fluctuating internal pressure, and
   wherein said elongate reinforcing member has a cross sectional area, measured from the outer perimeter, less than 10% of the cross sectional area of the bore of said flexible conduit.

2. A limb for a breathing circuit as claimed in claim 1, wherein said elongate reinforcing member does not include a passageway large enough for gases delivery to a patient.

3. A limb for a breathing circuit as claimed in claim 1, wherein said elongate reinforcing member is hollow, and said hollow elongate reinforcing member is blind terminated at each end by said first connector and said second connector.

4. A limb for a breathing circuit as claimed in claim 1, wherein said elongate reinforcing member has a solid, substantially circular cross section, and two ends.

5. A limb for a breathing circuit as claimed in claim 1, wherein said elongate reinforcing member includes a positive temperature coefficient heating element.

6. A limb for a breathing circuit as claimed in claim 1, wherein said elongate reinforcing member includes a resistance heating element.

7. A limb for a breathing circuit as claimed in claim 1, wherein the length of said elongate reinforcing member is between 100.5% and 105% of the length of said flexible conduit.

8. A limb for a breathing circuit as claimed in claim 1, wherein said limb includes a helical rib and a first end suitable for making connection with auxiliary equipment and a second end for making connection with a breathing conduit, and
   an annular shoulder between said first end and said second end,
   said second end extending along an axis and having a substantially circular cross section, and
   said second end having at least one protrusion on an outer surface for interlocking engagement with said helical rib.

9. A limb for a breathing circuit as claimed in claim 8, wherein said protrusion is an external thread having a pitch suitable for engagement with said helical rib.

10. A limb for a breathing circuit as claimed in claim 9, wherein said shoulder portion has an annular recess for receiving a securing collar having an extrusion axis.

11. A limb for a breathing circuit as claimed in claim 10, wherein said securing collar has a recess substantially parallel with said extrusion axis for receiving said elongate reinforcing member.

12. A limb for a breathing circuit as claimed in claim 8, wherein said second end has a recess substantially parallel with said axis for receiving said elongate reinforcing member.

13. A limb for a breathing circuit as claimed in claim 1, wherein said elongate reinforcing member is resilient and does not plastically deform in use, under normal flexing and bending of said limb.

14. A limb for a breathing circuit as claimed in claim 1, wherein said elongate reinforcing member has a cross sectional area between 3 mm$^2$ and 12.5 mm$^2$.

15. A limb for a breathing circuit as claimed in claim 1, wherein said elongate reinforcing member has a minimum bending stiffness between 693 N·mm$^2$ and 11096 N·mm$^2$.

16. A limb for a breathing circuit as claimed in claim 1, further comprising:
   a sheath surrounding said flexible conduit and being fixed at and around one end to said first connector and at and around its other end to said second connector.

17. A limb for a breathing circuit as claimed in claim 16, wherein said sheath is braided.

18. A limb for a breathing circuit as claimed in claim 17, wherein said sheath is braided from polyethylene terephthalate monofilaments.

19. A method for manufacturing a limb for a breathing circuit comprising:
   providing a conduit having a first end and a second end, said flexible conduit formed using a film having a thickness less than 50 μm,
   locating an elongate reinforcing member having a first end and a second end, lying freely within said flexible conduit, along a non-tortuous path from one end of said flexible conduit to the other end of said flexible conduit, said elongate reinforcing member having a cross sectional area, measured from the outer perimeter, less than 10% of the cross sectional area of the bore of said flexible conduit,
   fixing a first end connector with said first end of said flexible conduit, and said first end of said elongate reinforcing member, and
   fixing a second end connector with said second end of said flexible conduit and said second end of said elongate reinforcing member, such that said elongate reinforcing member reinforces said flexible conduit against contraction along the length of said flexible conduit due to fluctuating internal pressure.

20. A method for manufacturing a limb for a breathing circuit as claimed in claim 19, further including:
  locating a reinforcing mesh having a first and a second end, over the outside of said flexible conduit,
  fixing said first end connector with said first end of said flexible conduit, and said first end of said reinforcing mesh, and
  fixing said second end connector with said second end of said flexible conduit and said second end of said reinforcing mesh.

* * * * *